United States Patent [19]

Nichols et al.

[11] Patent Number: 5,089,645
[45] Date of Patent: Feb. 18, 1992

[54] HYDROXYL-CONTAINING ORGANOTIN CATALYSTS FOR MAKING POLYURETHANES

[75] Inventors: James D. Nichols; John B. Dickenson, both of Fogelsville, Pa.

[73] Assignee: Air Products and Chemicals, Inc., Allentown, Pa.

[21] Appl. No.: 628,261

[22] Filed: Dec. 17, 1990

Related U.S. Application Data

[63] Continuation-in-part of Ser. No. 405,700, Sep. 11, 1989, Pat. No. 4,987,244, and a continuation-in-part of Ser. No. 424,778, Oct. 20, 1989, and a continuation-in-part of Ser. No. 424,855, Oct. 20, 1989.

[51] Int. Cl.$^5$ .................................................. C07F 7/22
[52] U.S. Cl. ........................................ 156/90; 528/45; 528/51; 528/89; 528/126; 528/128; 521/118; 521/126; 521/180
[58] Field of Search ..................... 528/45, 51, 89, 126, 528/128; 521/118, 126, 180; 556/90

[56] References Cited

U.S. PATENT DOCUMENTS

| | | | |
|---|---|---|---|
| 3,392,128 | 7/1968 | Hostettler et al. | 528/58 |
| 3,582,501 | 6/1971 | Hostettler et al. | 521/126 |
| 3,836,488 | 9/1974 | Pruitt et al. | 521/124 |
| 3,922,253 | 12/1975 | Jerabek et al. | 528/45 |
| 3,980,579 | 9/1976 | Syrop et al. | 252/182 |
| 4,031,050 | 6/1977 | Jerabek | 128/45 |
| 4,104,147 | 8/1978 | Marchetti | 204/181 |
| 4,119,585 | 10/1978 | Kenney et al. | 521/118 |
| 4,254,017 | 3/1981 | Dworkin et al. | 524/180 |
| 4,286,073 | 8/1981 | Coe | 521/126 |
| 4,314,934 | 2/1982 | Smith et al. | 524/180 |
| 4,419,467 | 12/1983 | Wismer et al. | 523/414 |
| 4,816,593 | 3/1989 | Modi et al. | 556/89 |
| 4,987,244 | 1/1991 | Nichols et al. | 556/90 |

FOREIGN PATENT DOCUMENTS

0059632  8/1982  European Pat. Off.

OTHER PUBLICATIONS

Bates, Paul A., Hursthouse, Michael B. "The Structure of 2,2-Dialkyl-1,3,2-Oxathiastannolanes"-Journal of Organometallic Chemistry, 325 (1987), 129-139.
Yakoo, Makato, "Tetraalkyldistannoxones as Catalysts for Urethane Formation", Polymer Letters, vol. 5, pp. 57-63, (1967).

Primary Examiner—Maurice J. Welsh
Assistant Examiner—Duc Truong
Attorney, Agent, or Firm—Michael Leach; James C. Simmons; William F. Marsh

[57] ABSTRACT

Useful as catalysts for the reaction of a polyisocyanate or a partially blocked polyisocyanate with a hydroxyl-containing compound are hydroxyl-containing organotins such as, for example, compounds of formulas I-III $$R_2Sn[X-R^1-OH]_2 \quad\quad \text{I}$$

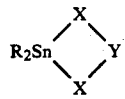

II $$R_2Sn[O_2C(Y')_nCO_2-Z-OH]_2 \quad\quad \text{III}$$

where
R is a $C_1$-$C_8$ alkyl or an aryl group;
$R^1$ is a $C_2$-$C_{22}$ divalent hydrocarbyl group which may contain a hydroxyl substituent;
X is a linking group which may be —O—, —S— or —$O_2C$—;
Y is a hydroxyl-containing $C_3$-$C_5$ alkylene group;
Y' is a $C_1$-$C_9$ divalent hydrocarbyl group;
Z is divalent organic linking group; and
n is 0 or 1.

Suitable hydroxyl-containing organotin compounds would also include polymeric organotin compounds prepared by the reaction of a diorganotin oxide or diorganotin dichloride with $HSCH_2CH(OH)CH_2XH$, preferably in a 1:0.5-1 molar ratio, where X is —S— or —O—.

6 Claims, No Drawings

HYDROXYL-CONTAINING ORGANOTIN CATALYSTS FOR MAKING POLYURETHANES

CROSS-REFERENCE TO RELATED APPLICATIONS

The present application is a continuation-in-part of application Ser. No. 07/405,700 filed Sept. 11, 1989, U.S. Pat. No. 4,987,244, Ser. No. 07/424,778 filed Oct. 20, 1989 and Ser. No. 07/424,855 filed Oct. 20, 1989 all of which are assigned to the assignee of the present application and are incorporated by reference into this application.

TECHNICAL FIELD

The present invention relates to catalyst compositions for curing polymeric compositions. More particularly, this invention relates to compositions for catalyzing the curing of polymer compositions containing hydroxyl and isocyanate groups.

BACKGROUND OF THE INVENTION

The preparation of polyurethane coatings by reacting organic isocyanates with compounds, especially polyols, containing reactive hydrogen atoms, as determined by the Zerewittenoff reaction, is well-known in the art. These reactions are conventionally carried out in the presence of tertiary amine catalysts and/or organotin catalysts.

One well-known method for curing polymer compositions is to react a polymer containing pendant hydroxyl groups with a blocked polyfunctional isocyanate. Alternatively, both hydroxyl and blocked isocyanate groups can be present on the same polymer. An isocyanate group can be blocked by reacting it with an active hydrogen-containing compound, such as an alcohol or phenol. When a polymer composition containing hydroxyl and blocked isocyanate groups is heated to above 100° C., the blocking reaction reverses, freeing the isocyanate groups which then react with the hydroxyl groups to form a crosslinked structure.

The use of organic and inorganic tin compounds to cure coating compositions containing hydroxyl and blocked isocyanate groups is disclosed in GB A 994,348. The preferred tin compounds include stannous octoate, stannic chloride, butyltin trichloride, dibutyltin dilaurate, di(2-ethylhexyl)tin oxide and dibutyltin dibutoxide.

The use of blocked isocyanate groups to cure coatings formed from aqueous dispersions of certain hydroxyl-containing polymers is disclosed in U.S. Pat. No. 4,031,050. The polyerms are reaction products of an epoxide-containing polymer and a primary and/or secondary amine. This patent discloses that catalysts conventionally employed for the reaction between isocyanates and hydroxyl-containing compounds to form urethane groups may be required, depending upon the reagent employed to form the blocked isocyanate.

Inorganic and organic tin compounds are among the most effective catalysts for the reaction of isocyanates with hydroxyl compounds, particularly alcohols and polyols. Tin compounds frequently employed for this purpose include stannous 2-ethylhexanoate (also referred to as stannous octoate), dibutyltin dilaurate, dibutyltin-bis(dodecyl mercaptan) and dibutyltin oxide (DBTO). Other typical organotin compounds employed or proposed for use as catalysts or co-catalysts in urethane-forming reactions are disclosed for example, in U.S. Pat. Nos. 3,582,501; 3,836,488; 4,119,585. U.S. Pat. No. 3,392,128 discloses the use of dibutyltin sulfonamide and U.S. Pat. No. 3,980,579 discloses a number of dialkyltin thio carboxylates.

Though organotin compounds that are used extensively in polyurethane coatings are effective, there are serious problems associated with the use of these materials. Most currently used organotin compounds are volatile, thus presenting problems regarding atmospheric emissions of toxic materials. There is also the need for hydrolytically stable and system compatible catalysts that can be employed with one component, water-based, urethane emulsions coating systems.

For example, the use of organotin compounds in polyurethane formulations results in these organotin compounds being hydrolyzed in the presence of water with resulting decrease in catalytic activity and system compatibility. The problem is particularly evident in cationic electrodepositable (CED) compositions in which the aqueous coating compositions comprise the reaction product of a partially blocked organic polyisocyanate, an amine adduct of an epoxy group-containing resin and a catalyst for urethane formation. (See U.S. Pat. No. 3,922,253).

Tin oxides are frequently used with polyurethane emulsion coatings. However, there are the same two major problems associated with their use; namely, poor emulsion stability and volatility.

U.S. Pat. No. 4,286,073 discloses hydrolytically stable premix compositons for preparation of urethane foams employing as the organotin catalyst a di- or trialkyltin sulfonate.

EP 059,632 B discloses compositions for catalyzing the reaction between blocked isocyanate groups and hydroxyl groups bonded to organic molecules, the compositions comprising a tin-containing urethane catalyst and a metal compound, which is a salt or chelated coordination complex of copper II, zinc II, nickel II, iron II, cobalt II, or vanadium II.

U.S. Pat. No. 3,980,579 discloses a catalytically stabilized polyol composition for use in the preparation of polyurethane foam which comprises a halogen-containing polyol, an amine catalyst and a sulfur-containing organotin compound.

U.S. Pat. No. 4,254,017 discloses organotin compounds containing at least one sulfur atom that is bonded exclusively to tin or to tin and hydrogen. The compounds are derivatives of mercaptoalkanols, which are present as the free alcohols, as esters of polycarboxylic acids, esters of acids containing specified non-metallic elements or as alkoxides of specified metallic elements. The compounds are effective catalysts for a variety of reactions and impart each stability to halogen-containing resins.

U.S. Pat. No. 4,314,934 discloses compositions which are effective in stablizing polymers against the deteriorative effects of heat comprising (1) an organic tin compound or a mixture of organic tin compounds and (2) an organic compounds or mixture of organic compounds having an aromatic ring which is substituted with hydroxy and mercapto groups ortho to each other.

U.S. Pat. No. 4,816,593 discloses heterocyclic, monoorganotin compounds useful as stabilizers for polyvinyl chloride.

M. Yokoo, et al., *Polymer Letters*, vol. 5, pp. 57–63 (1967) discloses tetraalkyldistannoxanes as catalysts for urethane formation.

P. A. Bates, et al., *Journal of Organometallic Chemistry*, 325, pp. 129-139 (1987) discloses 2,2-dialkyl-1,3,2-oxathiastannolanes.

SUMMARY OF THE INVENTION

The present invention provides organotin compounds containing a free hydroxyl group for catalyzing the reaction of an isocyanate or blocked ixocyanate functionality with a reactive hydrogen-containing compound, for example in polyurethane coating and foam compositions. Illustrative of suitable hydroxyl-containing organotin catalysts would be compounds of the following general formulas:

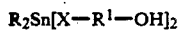  I

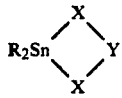  II

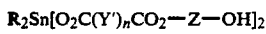  III where
R is a $C_1$-$C_8$ alkyl or an aryl group;
$R^1$ is a $C_2$-$C_{22}$ divalent hydrocarbyl group which may contain a hydroxyl substituent;
X is a linking group which may be —O—, —S— or —$O_2$C—;
Y is a hydroxyl-containing $C_3$-$C_5$ alkylene group;
Y' is a $C_1$-$C_9$ divalent hydrocarbyl group;
Z is divalent organic linking group; and
n is 0 or 1.

Suitable hydroxyl-containing organotin compounds would also include polymeric organotin compounds prepared by the reaction of a diorganotin oxide or diorganotin dichloride with $HSCH_2CH(OH)CH_2XH$, preferably in a 1:0.5-) molar ratio, where X is —S— or —O—.

The use of hydroxyl-containing organotin compounds can solve the problems of catalyst volatility and emulsion stability by becoming chemically bound via the hydroxyl functionality to one or more of the components contained in the polyurethane coating formulation.

In addition to effectively catalyzing the OH/NCO reaction, the organotin compounds, in many cases, are either hydrolytically stable or their susceptibility to hydrolysis is lessened when chemically bound to the coating resin component.

Another embodiment of the invention is a polyurethane coating composition comprising a polyisocyanate, a polyol and a hydroxyl-containing organotin compound.

Yet another embodiment is a cationic electrodepositable composition comprising an at least partially-blocked polyisocyanate, an amine adduct of an epoxy group-containing resin and a hydroxyl-containing organotin compound.

A further embodiment of the invention is a polyurethane foam composition comprising polyisocyanate, polyol, a hydroxyl-containing organotin compound, optionally an amine catalyst, and a blowing agent such as water or halocarbon (chlorofluorocarbon).

DETAILED DESCRIPTION OF THE INVENTION

The hydroxyl-containing organotin catalysts used in the invention can be a compound according to any of the following formulas I-III:

  I where
R is a $C_1$-$C_8$ alkyl group, preferably n-butyl or octyl, or an aryl group, preferably phenyl;
$R^1$ is a $C_2$-$C_{22}$ divalent hydrocarbyl group, for example, alkylene, arylene and alkarylene, preferably ethylene, propylene, butylene,

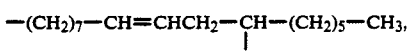

phenylene [—$C_6H_4$—], —$CH_2$—$C_6H_4$—, —$CH_2CH_2$—$C_6H_4$—, and —$CH_2CH_2CH_2C_6H_4$—, which hydrocarbyl group may also contain a hydroxyl substituent; and
X is a linking group which may be —O—, —S— or —$O_2$C—.

When the linking group X is —O— or —S—, it is preferred that $R^1$ be a hydroxyl substituted $C_3$-$C_5$ alkylene group such as —$CH_2CH(OH)$—$CH_2$—. When the linking group X is —$O_2C$—, it is preferred that $R^1$ be —$(CH_2)_n$—$C_6H_4$— where n=0-3.

A general procedure for preparing the diorganotin bis-carboxylates, diorganotin bis-alkoxides and diorganotin bis-mercaptides of the above general formula would involve charging a mixture of diorganotin oxide ($R_2SnO$), the appropriate carboxylic acid ($HOR^1CO_2H$), alcohol ($HOR^1OH$) or mercaptan ($HOR^1SH$), and a solvent such as toluene to a reaction vessel and heating the reaction mixture to reflux temperature until the water of reaction has been removed by distillation. The organic solvent can then be evaporated to afford essentially quantitative product yields of the diorganotin bis-carboxylate, bis-alkoxide or bis-mercaptide.

The hydroxyl-containing diorganotin catalyst suitably may also be a compound of the following general formula:

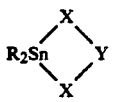  II where
R is a $C_1$-$C_8$ alkyl group, preferably n-butyl or octyl, or an aryl group, preferably phenyl;
Y is

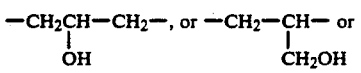

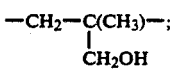

and

X is a linking group which may be —O—, —S— or —O₂C—.

A general procedure for preparing the 2,2-diorganotin-1,3-dithia-; -1,3-dioxa-; or -1,3-oxathiacycloalanes would involve charging a mixture of the organotin oxide (R₂SnO), the appropriate alcohol, mercaptan, carboxylic acid or hydroxyalkyl mercaptan and a solvent such as toluene to a reaction vessel and heating the reaction mixture to reflux temperature until all the water of reaction has been removed by distillation. The organic solvent can then be evaporated to afford essentially quantitative product yields of the hydroxy-containing diorganotin cycloalkane.

When using refluxing toluene, it is desirable to keep the reaction period short (under about 1 hour) to maximize the cyclic product and minimize the possible conversion to linear polymeric material.

The hydroxyl-containing diorganotin compound may also suitably be an organotin compound of the following general formula:

$$R_2Sn[O_2C(Y')_nCO_2-Z-OH]_2 \qquad III$$

where

R is a $C_1-C_8$ alkyl group, preferably n-butyl or octyl, or an aryl group, preferably phenyl;

Y' is a $C_1-C_9$ divalent hydrocarbyl group, for example, alkylene, alkenylene, arylene and alkarylene, preferably methylene, ethylene, propylene, butylene, cis or trans ethenylene, and 1,2-; 1,3-; or 1,4-phenylene [—C₆H₄—];

Z is a divalent organic linking group; and n is 0 or 1.

It is preferred that the linking group Z be a divalent mono- or poly(alkyleneoxy) group such as —[OCH₂CH₂]ₘ— or —[OCH(CH₃)CH₂]ₘ—, where m is 1-5; or a divalent bis[mono- or poly(alkyleneoxy)alkylamine], where the alkyl group contains from 1 to 22 carbon atoms and preferably is a fatty group and the divalent mono- or poly(alkyleneoxy) group is —[OCH₂CH₂]ₘ— or —[OCH(CH₃)CH₂]ₘ— and m is 1-5.

A general procedure for preparing the diorganotin catalysts of the above general formula III would involve charging a mixture of the appropriate dicarboxylic acid [HO₂C(Y)ₙCO₂H] or its anhydride and the appropriate dihydroxyl containing organic linking compound (HO—Z—OH) to a reaction vessel in equimolar quantities and heating under an inert atmosphere to form the monoester followed by reaction with diorganotin oxide (R₂SnO) in a solvent such as toluene by heating to reflux temperature until the water of reaction has been removed by distillation. The organic solvent can then be evaporated to afford essentially quantitative product yields of the diorganotin catalyst.

Suitable dicarboxylic acids include oxalic acid, malonic acid, succinic acid, glutaric acid, adipic acid, pimelic acid, suberic acid, azelaic acid, sebacic acid, maleic acid, fumaric acid, and phthalic, isophthalic and terephthalic acids. Suitable dihycroxyl containing organic linking compounds include ethylene glycol, proplyene glycol, polyethylene glycols, polypropylene glycols, bis(hydroxyethyl) alkylamine, bis(2-hydroxypropyl) alkylamine, bis(polyethoxylated) alkylamine and bis(polypropoxylated) alkylamine.

The polymeric hydroxyl-containing organotin catalysts suitably used are prepared by reacting about 0.5 to 1- moles of HSCH₂CH(OH)CH₂OH or HSCH₂CH(OH)CH₂SH per mole of R₂SnO or R₂CnCl₂ where R is a $C_1-C_8$ alkyl group, preferably n-butyl or octyl, or an aryl group, preferably phenyl.

The polymeric reaction product would contain repeating units of the formula

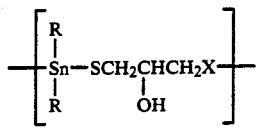

where R and X are as defined above It is also possible that the product may contain minor amounts of the units

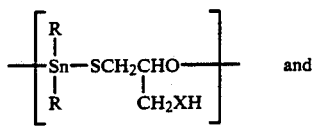 and

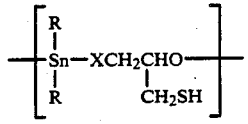

A general procedure for preparing the polymeric diorganotin compounds would involve charging a mixture of the diorganotin oxide (R₂SnO) or diorganotin dichloride (R₂SnCl₂), the appropriate hydroxymercaptan and a solvent such as toluene to a reaction vessel and heating the reaction mixture to reflux temperature until all the water of reaction has been removed by distillation. The organic solvent can then be evaporated to afford essentially quantitative produce yields of the polymeric diorganotin catalyst.

When using refluxing toluene, it is desirable to keep the reaction period at least about 3 hours to maximize the conversion to linear polymeric material and minimize the yield of cyclic product.

Contemplated as the functional, or operative, equivalent to the diorganotin dichloride for purposes of this invention is the diorganotin dibromide.

A catalytically effective amount of the hydroxyl-containing organotin catalyst is used in a polyurethane formulation comprising polyisocyanate and a polyether or polyester polyol. Specifically, suitable amounts of the catalyst may range from about 0.1 to 2 parts, preferably 0.25 to 1 parts, per 100 parts by wt polyol in the polyurethane coating or foam formulation.

Examples of suitable polyisocyanates are hexamethylene diisocyanate, phenylenediisocyanate, toluenediisocyanate, and 4,4'-diphenylmethanediisocyanate. Especially suitable are the 2,4- and 2,6-toluenediisocyanates individually or together as their commercially available mixtures, Other suitable mixtures of diisocyanates are those known commercially as "crude MDI", also known as PAPI, which contain about 60% of 4,4'-diphenylmethanediisocyanate along with other isomeric and analogous higher polyisocyanates. Also suitable are "prepolymers" of these polyisocyanates comprising a partially prereacted mixture of polyisocyanates and of polyether or polyester polyol.

Illustrative of suitable polyols as a component of the polyurethane coating compositions catalyzed by the diorganotin compounds of the invention are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from poyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane, hexane diol and like low molecular weight polyols.

Useful polyester polyols include those produced by reacting a carboxylic acid with an excess of a diol; for example, adipic acid with ethylene glycol or butane diol, or reacting a lactone with an excess of a diol, such as caprolactone and propylene glycol.

Other typical components in a polyurethane foam composition include a blowing agent such as water and/or halocarbon and optionally cell stabilizer, crosslinker and amine catalyst.

Other typical components found in polyurethane coating compositons include emulsifier, pigment and solvent.

A general water-based polyurethane coating formulation containing a diorganotin compound of the invention would comprise the following: polyol, blocked polyisocyanate (TDI and/or MDI), organic or inorganic acid, crosslinker, pigment and water.

A cationic electrodepositable (CED) polyurethane coating composition would comprise an aqueous dispersion of a cationic resin and an at least partially blocked polyisocyanate compound, a tin catalyst according to the present invention and, optionally, pigment and a coalescing solvent. The cationic resin is usually the reaction product of a polyepoxide resin with a monoamine, particularly tertiary and secondary amines which desirably contain hydroxyl functionality. The polyepoxide resin may also be reacted with the partially blocked organic polyisocyanate and/or a polyester polyol or polyether polyol prior to or after reaction with the monoamine.

A catalytically effective amount of the diorganotin catalyst of the invention is used in the CED polyurethane coating composition. Suitable amounts of the catalyst may range from about 0.5 to 5 parts per 100 parts by wt resin.

The polyepoxides, which can be used in the CED compositions are polymers having a 1,2-epoxy equivalency greater than 1 and preferably about 2. The preferred polyepoxides are polyglycidyl ethers of polyhydric phenols, such as bis-phenol A. The polyepoxides have a molecular weight of at least 200 and preferably within a range of 200-2000 and, more preferably, about 340-2000.

Examples of suitable polyester polyols are those which are formed by reacting a dicarboxylic acid or acid anhydride such as adipic acid, succinic acid or anhydride with a polyol such as butanediol, hexanediol or polyethylene glycol. Commercially available products are sold under the trademarks Mobay E-365 and E-604.

Examples of suitable polyether polyols are those which are formed by reacting a cyclic polyol with ethylene oxide or optionally with a mixture of ethylene oxide and an alkylene oxide having 3 to 4 carbon atoms in the alkylene chain. Examples of the cyclic polyols which can be used are polyhydric phenols and cyloaliphatic polyols. The cyclic polyol-alkylene oxide condensate is preferably difunctional or trifunctional and the equivalent ratio of cyclic polyol to alkylene oxide should be within the range of 1:3 to 20.

The partially blocked organic polyisocyanate which may be employed in preparing the CED compositions may be any polyisocyanate where a portion of the isocyanate groups have been reacted with a compound so that the resultant capped isocyanate portion is stable to hydroxyl or amine groups at room temperature but reactive with hydroxyl or amine groups at elevated temperatures, usually between about 200° and 600° F.

In the preparation of the partially blocked polyisocyanate, any suitable organic polyisocyanate may be used. In addition, the organic polyisocyanate may be a prepolymer derived from a polyol, including polyether polyol or polyester polyol, which are reacted with excess polyisocyanate to form isocyanate-terminated prepolymers. Any suitable aliphatic, cycloaliphatic or aromatic alkyl monoalcohol may be used as a blocking agent.

The electrodepositable compositions may also contain a coalescing solvent, a pigment composition of any of the conventional types, plasticizers, surfactants or wetting agents.

For more information and detail about the components that compose cationic electrodepositable compositions, the relative amounts of these components and the method of their preparation and use, see U.S. Pat. Nos. 3,922,253; 4,104,147 and 4,419,467 which are hereby incorporated by reference.

EXAMPLE 1

Dibutyltin bis(4-hydroxyphenylacetate)

A mixture of 24.9 g (0.10 moles) dibutyltin oxide, 30.4 g (0.20 mole) 4-hydroxyphenylacetic acid, and 300 ml toluene were charged to a 3-necked round bottom flask equipped with a stirrer, thermocouple or thermometer, and condenser with a DEAN-STARK water trap, and heated at reflux temperature until all the water of reaction was collected in the trap. The toluene was removed using a flash evaporator to yield 53 g (99%) of dibutyltin bis(4-hydroxyphenyl acetate) having a melting point of 121°-126° C.

EXAMPLE 2

Dibutyltin bis[3-(4-hydroxyphenyl)propionate]

Following the procedure of Example 1, dibutyltin oxide was reacted with 33.2 g (0.2 mole) 3-(4-hydroxyphenyl)propionic acid to yield 56 g of dibutyltin bis[3-(4-hydroxyphenyl)propionate], a white crystalline material melting at 48°-50° C.

EXAMPLE 3

Dibutyltin bis(2,3-dihydroxypropylmercaptide)

A mixture of 24.9 g (0.10 mole) dibutyltin dioxide, 21.6 g (0.20 mole) 3-mercapto-1,2-propanediol and 300 ml toluene were reacted as described in Example 1. Removal of the toluene yielded 44.5 g (99.5%) of dibutyltin bis(2,3-dihydroxypropylmercaptide), $(C_4H_9)_2Sn[SCH_2CH(OH)CH_2OH]_2$. The product was a straw-colored viscous liquid.

EXAMPLE 4

Dibutyltin bis(2-hydroxyethylmercaptide)

The procedure of Example 3 was followed, except that 15.6 g (0.2 mole) 2-mercaptoethanol, was used to yield 38 g (98%) of dibutyltin bis(2-hydroxyethylmercaptide) $(C_4H_9)_2 Sn[SCH_2CH_2OH]_2$. The product was a light yellow liquid.

EXAMPLE 5

Dibutyltin bis(4-hydroxyphenylmercaptide)

The procedure of Example 3 was followed, except that 25.2 g (0.20 mole) a4-mercaptophenol was used to provide 46 g (95%) of dibutyltin bis(4-hydroxyphenylmercaptide), $(C_4H_9)_2 Sn[SC_6H_4OH]_2$, which was an amber liquid.

EXAMPLE 6

2,2-Dibutyltin-1,3-oxathiacyclohexan-5-ol

A mixture of 24.9 g (0.10 mole) dibutyltin oxide, 10.8 g (0.10 mole) 3-mercapto-1,2-propanediol, and 300 ml toluene were charged to a 3- necked round bottom flask equipped with a stirrer, thermometer, and condenser with a DEAN-STARK water trap, and heated at reflux temperature until all the water of reaction was collected in the trap. The toluene was removed using a flash evaporator to yield 33 g (97%) of 2,2-dibutyltin-1,3-oxathiacyclohexan-5-ol, a white crystalline solid having a melting point of 90°–91° C.

EXAMPLE 7

2,2-Dibutyltin-1,3-oxathiacyclopentane

Following the procedure of Example 1, 24.9 g (0.1 mole) dibutyltin oxide was reacted with 7.8 g (0.1 mole) 2-mercaptoethanol to yield 30 g of 2,2-dibutyltin-1,3-oxathiacyclopentane, a white cyrstalline material melting at 80°–82° C.

EXAMPLE 8

Polymeric Hydroxyl-Containing Organotin

A mixture of 37.35 g (0.15 mole) dibutyltin oxide and 300 ml toluene were charged to a 3-necked round bottom flask equipped with a stirrer, thermometer, and condenser with a DEAN-STARK water trap; 10.8 g (0.1 mole) 3-mercapto-1,2-propanediol were added in three aliquots to the dibutyltin oxide/tolene mixture over a 30 min. period while heating to reflux temperature. Heating was continued at reflux temperature until all the water of reaction was collected in the trap and for about 3 hours more. The toluene was removed using a flash evaporator to yield 40 g (95%) of a viscous polymeric material.

EXAMPLE 9

The organotin catalysts of Examples 1-8 were evaluated as catalysts for the isocyanate-hydroxyl reaction according to the following gelation test. A solution of the hydroxyl-containing organotin compound (0.5 mole %) in 9 g solvent (dioxane or methylisobutylketone) was prepared. To this solution was added 159 g of a poly(oxyalkylene)triol (Mobay Multranol E-9143, OH number =35), and after thoroughly mixing, 8.5 g toluene diisocyanate (80/20 ratio of 2,4/2,6 isomer mixture) was added to the catalyst/triol solution and mixed for 30 seconds. A small test tube was filled with the mixture, sealed and immediately placed in a constant temperature bath (25°, 50° or 70° C.). The time required to mix, fill the test tube, seal it and place it in the bath was 1.0 min. for each test. The gel time was measured from the instant the tube was placed in the bath, and was taken as the time when the mixture would no longer visibly flow in the inverted tube. The geletion time was interpreted as a measure of the speed of the isocyanate-hydroxyl reaction in the mixture.

Table 1 shows the results of the gelation test.

TABLE 1

| Organotin Compound | Gel Point (Minutes) | | |
|---|---|---|---|
| | 25° C. | 50° C. | 70° C. |
| 1 | 16.3 | — | 2.4 |
| 2 | 12.9 | — | 2.3 |
| 3 | 12.9 | 4.6 | — |
| 4 | 14.0 | 5.2 | — |
| 5 | 25.3 | 8.3 | — |
| 6 | 7.9 | 4.3 | — |
| 7 | 17.2 | 5.5 | — |
| 8 | 10.2 | 6.5 | — |
| DBTO | >240 | 20 | 4.5 |
| T-1* | 13.0 | 5.5 | 2.4 |

*T-1 = dibutyltin diacetate

The data in Table 1 shows that the hydroxyl-containing organotin compounds 1-8 all catalyzed the isocyanate/hydroxyl reaction.

EXAMPLE 10

Each of the hydroxyl-containing organotin compounds 1-8 were evaluated for hydrolysis stability. The test conditions simulate the conditions encountered by the catalyst in an aqueous polyurethane coating bath such as a CED bath.

5.0 g of a 10% solution of the hydroxyl-containing organotin compound in toluene was added to a test tube containing 20 ml dilute acetic acid, pH 6.5. The contents, which form two immiscible phases, were mixed by inverting the tube several times and then allowed to stand at ambient temperature. Hydrolytic stability under these conditions was measured by the time (days) required for the appearance of a precipitate (the hydrolysis product which is insoluble in both phases) at the toluene-acetic acid interface. The results of this hydrolysis stability test are shown in Table 2.

TABLE 2

| Organotin Compound | Precipitate | Time (days) |
|---|---|---|
| 1 | Yes | 3 |
| 2 | Yes | 62 |
| 3 | No | >200 |
| 4 | No | >200 |
| 5 | No | >200 |
| 6 | No | >200 |
| 7 | No | >200 |
| 8 | No | >200 |
| T-1 | Yes | <1 |

The hydrolytic stability data shows that each of the hydroxyl-containing organotin compounds demonstrated improved hydrolytic stability compared to T-1 catalyst. Compounds 3-8 did not produce a precipitate after 200 of testing.

EXAMPLE 11

Dibutyltin bis(mono-triethylene glycol succinate)

A mixture. of dibutyltin oxide, 24.9 g (0.10 mole), mono-triethylene glycol succinate, 50 g (0.20 mole), and 250 ml toluene was charged to a round-bottom flask (fitted with a mechanical stirrer, thermocouple, and condenser with a Dean-Stark water trap) and heated with stirring at reflux temperature until all water of reaction was collected in the trap. Removal of toluene (flash evaporater) yielded 73 g of a liquid product containing 80-90% of the title compound.

EXAMPLE 12

Dibutyltin bis(2-{N-tallow-N-(2-hydroxyethyl)]aminoethylsuccinate}

A mixture of succinic anhydride, 25 g (0.25 mole), and N,N,-bis(2-hydroxyethyl)-N-tallowamine (Ethomeen T12, AKZO Chemie), 91.5 g (0.25 mole) was charged to a 1-liter round-bottom flask (fitted with a mechanical stirrer, thermocouple and condenser with a Dean-Stark water trap) and heated with stirring at 100 C for 2 hrs; 200 ml toluene and 31.1 g (0.125 mole) dibutyltin oxide was added to the reaction flask containing the succinate (clear yellow liquid) and the resultant mixture heated with stirring at reflux until all water of reaction was collected in the trap. Removal of toluene (flash evaporator) yielded 141 g (97%) of the title compound, a viscous brown liquid.

EXAMPLE 13

Dibutyltin bis{3-[N-tallow-N-(2-hydroxypropyl)amino]-2-propyl-succinate}

A mixture of 98.25 g (0.25 mole) N,N-bix(3-hydroxy-2-propyl)-N-tallowamine (propomeen T12, AKZO Chemie) and 25 g succinic anhydride was reacted with 31.1 g dibutyltin oxide in 200 ml toluene as described in Example 12. Removal of toluene yielded 150 g (99% yield) of the title compound, a dark brown viscous liquid.

EXAMPLE 14

Dibutylin bis{2-[N-tallow-N-(polyoxyethylene)]aminoethylsuccinate

Bu$_2$Sn[O$_2$CCH$_2$CH$_2$CO$_2$CH$_2$CH$_2$(OCH$_2$CH$_2$)xN(R)(CH$_2$CH$_2$O)yH]$_2$

A mixture of 124.25 g (0.25 mole) N-tallow-N,N-bis(-polyoxyethylene)amine (Ethomeen T15, AKZO Chemie) and 25 g succinic anhydride was reacted with 31.1 g dibutyltin oxide in 200 ml toluene as described in Example 12. Removal of the toluene yielded 170 g (100% yield) of the title compound, a dark brown viscous liquid.

EXAMPLE 15

Dibutyltin bis(12-hydroxystearate)

Bu$_2$Sn[O$_2$C(CH$_2$)$_{10}$CH(OH)(CH$_2$$_5$(CH$_3$)$_2$

A mixture of dibutyltin oxide, 31.1 g (0.125 mole), 12-hydroxystearic acid, 75 g (0.25 mole) and 250 ml toluene was reacted as described in Example 11. Removal of toluene yielded 103 g (99% yield) of the title compound, a cream colored solid.

EXAMPLE 16

Dibutyltin bis(ricinoleate)

Bu$_2$Sn[O$_2$C(CH$_2$)$_7$CH=CHCH$_2$CH(OH)(CH$_2$)$_5$(CH$_3$)]$_2$

Following the procedure described in Example 11, ricinoleic acid, 74.25 g (0.25 mole) was reacted with dibutyltin oxide, 31.1 g (0.125 mole) in 250 ml toluene. Removal of the toluene yielded 120 g (94% yield) of the title compound, a yellow viscous liquid.

EXAMPLE 17

Dibutyltin bis[2,2-di(hydroxymethyl)propionate]

Bu$_2$Sn[O$_2$CC(CH$_2$OH)$_2$CH$_3$]$_2$

Following the procedure described in Example 11, 26.8 g (0.20 mole) 2,2-bis(hydroxymethyl)propionic acid was reacted with 24.9 g (0.10 mole) dibutyltin oxide in 200 ml toluene. Removal of the toluene yielded 48 g (96% yield) of the title compound, a white crystalline material melting at 157°-161° C.

EXAMPLE 18

2.2-Dibutyl-1,3-dioxa-5-hydroxymethyl-5-methyl-6-ketocyclohexylstannane

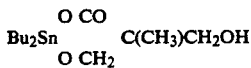

Following the procedure described in Example 11, 13.5 g (0.10 mole) 2,2-bis(hydroxymethyl)propionic acid was reacted with 24.9 g dibutyltin oxide in 200 ml toluene. Removal of the toluene yielded 33 g (90% yield) of the title compound, a white crystalline material at 212°-215° C.

EXAMPLE 19

Dibutyltin bis(2,3-dihydroxypropoxide)

Bu$_2$Sn[OCG$_2$CH(OH)CH$_2$OH]$_2$

Following the procedure described in Example 11, 37.2 g (0.40 mole) glycerol was reacted with 49.8 g (0.20 mole) dibutyltin oxide in 250 ml toluene. Removal of toluene yielded 82 g (98% yield) of the title compound, a white powder melting at 159°-165° C.

EXAMPLE 20

2,2-Dibutyl-1,3-dioxa-5-hydroxycyclohexylstannane

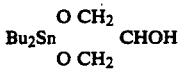

Following the procedure described in Example 11, 18.6 g (0.20 mole) glycerol was reacted with 49.8 g dibutyltin oxide in 250 ml toluene. Removal of the toluene yielded 78 g (100% yield) of the title compound, a white powder melting at 154°-160° C.

EXAMPLE 21

Dibutyltin(2,3-dihydroxypropylmercaptide)(2,3-dihydroxypropoxide)

Bu$_2$Sn[SCH$_2$CH(OH)CH$_2$OH][OCH$_2$CH(OH)CH$_2$OH]

Following the procedure described in Example 11, a mixture of 21.6 g (0.20 mole) 1-thioglycerol and 18.6 g (0.20 mole) glycerol was reacted with 49.8 g dibutyltin oxide in 250 ml toluene. Removal of the toluene yielded 78 g (90% yield) of the title compound, an opaque gummy solid.

EXAMPLE 22

Bis[di(2-hydroxymethylmercaptide)dibutyltin]oxide

[Bu$_2$Sn(SCH$_2$CH$_2$OH)]$_2$O

A mixture of 25 g (0.045 mole) bis[dichlorodibutyltin]oxide, 7.1 g (0.091 mole) 2-mercaptoethanol, 7.6 g (0.091 mole) sodium bicarbonate (in 25 ml water) and 1590 ml toluene was heated at reflux temperature for 3 hrs. The toluene solution was dried over anhydrous magnesium sulfate. Removal of the toluene yielded 20 g (80% yield) of the title compound.

EXAMPLE 23

Tributyltin(2,3-dihydroxypropylmercaptide)

Bu$_3$SnSCH$_2$CH(OH)CH$_2$OH

Sodium 2,3-dihydroxypropylmercaptide, 13 g (0.10 mole), in 50 ml water was slowly added to a rapidly stirred toluene (150 ml) solution of tributyltin chloride, 33.9 g (0.10 mole) contained in a round-bottom reactor flask (fitted with stirrer, thermocouple and condenser). The resultant mixture was stirred at 75° C. for 3 hrs. After drying the toluene was remove (flash evaporator) to yield 41 g (80% yield) of the title compound, a light tan oily liquid.

EXAMPLE 24

Butyltin tris(2,3-dihydroxypropylmercaptide)

BuSn[SCH$_2$CH(OH)CH$_2$OH]$_3$

Following the procedure described in Example 23, 39 g (0.30 mole) sodium 2,3-dihydroxypropylmercaptide was reacted with 29.7 g (0.10 mole) butyltin trichloride. Removal of the toluene yielded 30 g (52% yield) of the title compound, a pinkish viscous liquid.

EXAMPLE 25

Following the procedure of Example 9 the hydroxyl-containing organotin compounds of Examples 11–24 were evaluated as catalysts for the isocyanatehydroxyl reaction by the gelation test. Table 3 shows the results of the gelation test.

TABLE 3

| Tin Catalyst | Gel Point (minutes) | | | |
|---|---|---|---|---|
| | 25° C. mole % | | 50° C. mole % | |
| | 0.25 | 0.50 | 0.25 | 0.50 |
| 11 | >30 | 20.9 | 9.7 | 6.6 |
| 12 | >30 | >30 | 12.5 | 12.9 |
| 13 | >30 | >30 | 14.5 | 10.4 |
| 14 | >30 | >30 | 13.5 | 11.0 |
| 15 | >30 | >30 | 18.8 | 17.0 |
| 16 | >30 | 22.0 | 11.6 | 10.0 |
| 17 | >30 | >30 | 8.7 | 6.5 |
| 18 | >30 | >30 | 13.4 | 9.0 |
| 19 | >30 | 26.5 | >30 | 12.7 |
| 20 | >30 | 20.6 | >30 | 17.3 |
| 21 | >30 | 22.8 | >30 | 11.5 |
| 22 | >30 | 5.0 | 4.1 | 2.5 |
| 23 | >30 | 22.0 | 13.7 | 9.2 |
| 24 | >30 | 9.2 | 12.2 | 3.4 |

STATEMENT OF INDUSTRIAL APPLICATION

The hydroxyl-containing organotin compounds are useful as urethane catalysts in aqueous polyurethane coating and foam compositions, in particular, cationic electrodepositable polyurethane compositions.

We claim:

1. In a method for catalyzing the reaction of a polyisocyanate or an at least partially blocked polyisocyanate with a hydroxyl-containing compound in the presence of a catalyst, the improvement which comprises employing as the catalyst a hydroxyl-containing organotin compound.

2. The method of claim 1 in which the hydroxyl-containing organotin compound is a compound of one of the following formulas I–III

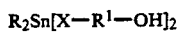   I

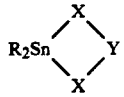   II

   III where

R is a $C_1$–$C_8$ alkyl or an aryl group;

R$^1$ is a $C_2$–$C_{22}$ divalent hydrocarbyl group which may contain a hydroxyl substituent;

X is a linking group which may be —O—, —S— or —O$_2$C—;

Y is a hydroxyl-containing $C_3$–$C_5$ alkylene group;

Y' is a $C_1$–$C_9$ divalent hydrocarbyl group;

Z is divalent organic linking group; and n is 0 or 1;

or a polymeric organotin compound prepared by the reaction of a diorganotin oxide or diorganotin dichloride with HSCH$_2$CH(OH)CH$_2$XH in a 1:0.5–1 molar ratio, where X is —S— or —O—.

3. In a polyurethane coating composition comprising a polyisocyanate, a polyol and a urethane catalyst, the improvement which comprises a hydroxyl-containing organotin compound as the urethane catalyst.

4. The polyurethane coating composition of claim 3 in which the hydroxyl-containing organotin compound is a compound of one of the following formulas I–III

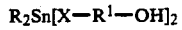   I

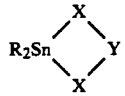   II

   III where

R is a $C_1$–$C_8$ alkyl or an aryl group;

R$^1$ is a $C_2$–$C_{22}$ divalent hydrocarbyl group which may contain a hydroxyl substituent;

X is a linking group which may be —O—, —S— or —O$_2$C—;

Y is a hydroxyl-containing $C_3$–$C_5$ alkylene group;

Y' is a $C_1$–$C_9$ divalent hydrocarbyl group;

Z is divalent organic linking group; and n is 0 or 1;

or a polymeric organotin compound prepared by the reaction of a diorganotin oxide or diorganotin dichloride with HSCH$_2$CH(OH)CH$_2$XH in a 1:0.5–1 molar ration, where X is —S— or —O—.

5. In a polyurethane foam composition comprising a polyisocyanates, a polyol, a blowing agent and optionally an amine catalyst, the improvement which comprises a hydroxyl-containing organotin compound.

6. The polyurethane foam composition of claim 5 in which the hydroxyl-containing organotin compound is a compound of one of the following formulas I-III

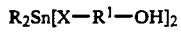   I

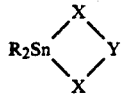   II

   III where

R is a $C_1$-$C_8$ alkyl or an aryl group;
R$^1$ is a $C_2$-$C_{22}$ divalent hydrocarbyl group which may contain a hydroxyl substituent;
X is a linking group which may be —O—, —S— or —$O_2$C—;
Y is a hydroxyl-containing $C_3$-$C_5$ alkylene group;
Y' is a $C_1$-$C_9$ divalent hydrocarbyl group;
Z is divalent organic linking group; and
n is 0 or 1;
or a polymeric organotin compound prepared by the reaction of a diorganotin oxide or diorganotin dichloride with $HSCH_2CH(OH)CH_2XH$ in a 1:0.5–1 molar ratio, where X is —S— or —O—.

* * * * *